United States Patent [19]
Christie et al.

[11] 3,981,679
[45] Sept. 21, 1976

[54] METHOD FOR DYEING THE JUTE BACKING OF MULTILEVEL NYLON CARPET WITHOUT STAINING THE NYLON FACE FIBERS

[75] Inventors: Nick J. Christie, Mendham; John Karnilaw, Parsippany, both of N.J.

[73] Assignee: Diamond Shamrock Corporation, Cleveland, Ohio

[22] Filed: May 21, 1975

[21] Appl. No.: 579,462

[52] U.S. Cl. .................................... 8/21 B; 8/169; 8/1 XB
[51] Int. Cl.² ........................................ D06P 3/874
[58] Field of Search .............. 8/84, 21 B, 169, 1 XB

[56] References Cited
UNITED STATES PATENTS

| | | | |
|---|---|---|---|
| 2,089,212 | 8/1937 | Kritchevsky | 8/87 X |
| 3,096,139 | 7/1963 | Hindle | 8/21 A |
| 3,391,985 | 7/1968 | Zurbuchen | 8/172 |
| 3,758,269 | 9/1973 | Bartsch | 8/1 XB |

OTHER PUBLICATIONS

Casty, Amer. Dyestuff Rep., 12/12/60, pp. 105–117.

Primary Examiner—Donald Levy
Attorney, Agent, or Firm—Theodore J. Dettling

[57] ABSTRACT

In dyeing the jute backing of carpet having multilevel nylon face fibers with cationic dyes, discernible staining of the face fibers is prevented by dyeing the jute in the presence of a stain-preventing quantity of particular imidazoline salts and imidazoline quaternary salts.

11 Claims, No Drawings

METHOD FOR DYEING THE JUTE BACKING OF MULTILEVEL NYLON CARPET WITHOUT STAINING THE NYLON FACE FIBERS

BACKGROUND OF THE INVENTION

This invention relates to a method for dyeing the jute backing of discernible nylon carpet without discernible staining of the nylon face fibers. More particularly, it relates to the use of particular imidazolines as a reserving agent for the face fibers of a multilevel nylon carpet having a jute backing to prevent or minimize their staining when the backing is dyed with cationic (basic) type dyestuffs.

Multi-colored nylon carpets are preferrably made by dyeing carpet having two or more different multilevel nylon face fibers with different colored anionic and cationic dyestuffs. Multilevel (or "differential-dyeable") nylon fibers are fibers made from polyamides having only either anionic or cationic groups (sometimes in different quantities so as to be dyeable to different shades) so as to be selectively dyeable with only dyestuffs of a particular class. Typically, the face fibers are dyed before the jute backing, which is after-dyed in a second operation with special cationic dyes at low temperatures, e.g. usually at 100°F. or less.

However, this procedure has had limited application because of the propensity of many jute dyes to cause an unacceptable degree of staining of the carpet face fibers. Recently it has been found that certain quaternary cationic surfactants would function as reserving agents for the multilevel nylon face fibers and yet permit satisfactory exhaust of the jute dye. A description of these cationic surfactants, the problems associated with producing jute-backed multi-colored nylon carpeting, and previous efforts to solve these problems, is provided in U.S. Pat. No. 3,758,269 and the article "Nylon Carpet" by Frederich Bartsch appearing in the September 1973 issue of *American Dyestuff Reporter*.

While these quaternary cationic surfactants are allegedly satisfactory, there still exists a need for alternative antistaining agents in view of the multitude of different nylon fibers and jute dyes employed in the carpet industry, and, further, considering the always present desire of the industry for materials of lower cost and/or toxicity.

SUMMARY OF THE INVENTION

Considering this state of the art, it is an object of the present invention to provide a new class of reserving agents that prevents discernible staining of the nylon face fibers of a jute-backed carpeting when the jute backing is dyed with cationic dyes.

This and still other objects and advantages, which will become apparent from the following description, are achieved by dyeing the jute backing of multi-colored nylon carpeting (made with multi-level nylon fibers) with cationic dyes in the presence of certain 1-hydroxyalkyl 2-hydrocarbyl imidazoline salts or quaternary salts, as hereinafter described, in a quantity preventing discernible staining of the face fibers. Maximum anti-staining is obtained by first treating the carpet with the invention imidazoline reserving agent before dyeing the jute.

DESCRIPTION OF THE PREFERRED EMBODIMENTS

The 1-hydroxyalkyl 2-hydrocarbyl imidazoline salts or quaternary salts, which it has been discovered function as reserving (anti-staining) agents when dyeing the jute backing of carpeting having a facing comprised of multilevel nylon fibers, have the general formula;

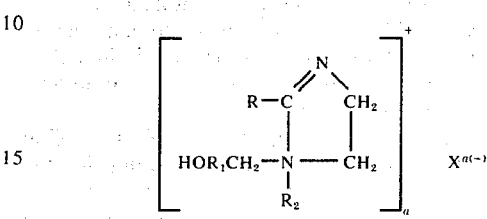

wherein:
R is a hydrocarbon radical having 15 to 17 carbon atoms,
$R_1$ is a

$R_2$ is hydrogen, an unsubstituted or hydroxy-substituted aliphatic hydrocarbon radical having 1 to 6 carbon atoms or a benzyl radical,
X equals a water-soluble anion, and
$a$ is a number equal to the ionic valence of the anion, X.

Compounds of this general formula are known and may be made by neutralizing (with a water-soluble organic or inorganic acid) or quaternizing (e.g. with a $C_1-C_6$ hydrocarbon or benzyl halide or sulfate) an imidazoline produced by the dehydration cyclization of an amide resulting from the reaction of a $C_{16}$ to $C_{18}$ aliphatic hydrocarbonoic acid and either 2-hydroxyethyl ethylene diamine or 2-hydroxyisopropyl ethylene diamine (e.g. see U.S. Pat. Nos. 2,268,273 and 3,669,608).

In the imidazoline compounds used in the invention process the $C_{15}-C_{17}$ aliphatic hydrocarbon radical, R, may be: saturated or unsaturated; linear, branched, or cyclic; and comprised of a mixture of the $C_{15}-C_{17}$ hydrocarbons. Illustrative of acids that may be used in producing the compounds and form the hydrocarbon radical thereof are palmitic, stearic, oleic, linoleic, linolenic, and tallow acids. As will be appreciated, the commercial technical grades of these and other acids, which may be used to produce the imidazoline compounds by the exemplary process hereinbefore described, normally contain considerable minor quantities of hydrocarbons outside the $C_{16}$ to $C_{18}$ range, and that, therefore, the imidazoline compounds prepared from such acids and used in the invention process may contain minor quantities of compounds having 2-hydrocarbyl groups having less than 15 carbons and/or more than 17 carbons.

$R_2$ is hydrogen when the imidazoline compounds used are produced by neutralization. Alternatively, $R_2$ may be any unsubstituted or hydroxysubstituted hydrocarbon radical having 1 to 6 carbon atoms that is linear, branched, or cyclic, and either saturated or unsaturated, or may be a benzyl radical when the imidazoline compounds used are produced by quaternization, as for example, with a $C_1-C_6$ hydrocarbon or benzyl halide or sulfate or with an active epoxide such as ethylene or propylene oxide.

The anion, X, is not particularly critical and may be any water-soluble anion that renders the imidazoline compound soluble in water at a concentration of at least about 5% total solids at 25°C, as, for example, $Cl^-$, $Br^-$, $I^-$, $SO_4^=$, $COO^-$, $CH_3—COO^-$, $PO_4^≡$, $C_2H_5SO_4^-$, $CH_3SO_4^-$ and like anions. Generally preferred, because of their lower costs and good water-solubilizing characteristics, are the chloride, sulfate, formate and acetate anions when the imidazoline salt is used; and the chloride, methosulfate, ethosulfate anions when the imidazoline quaternary is employed.

While, as a general rule, only one kind of imidazoline cation and only one kind of anion will comprise the imidazoline salt or quaternary used in the invention process, two or more different species of either or both may be employed if deemed desirable or necessary. Further, as the formula shows, when a polyvalent anion such as the sulfate anion is present, then the number of molecules of the imidazoline cation associated therewith equals the ionic valence, $a$, of the polyvalent anion.

In the invention process, the jute backing of carpeting containing multilevel nylon face fibers (usually predyed to the desired color style with cationic and anionic and/or disperse dyestuffs according to methods well known in the industry and not forming a part of the present invention) is dyed with cationic dyes (useful for dyeing jute and known to the art) in the presence of the imidazoline salts and/or imidazoline quaternaries, hereinbefore described, at a concentration and at a dyeing temperature preventing discernable staining of the nylon face fibers. By the expression "discernable staining" is meant that color shade changes in the face fibers are either nonexistant or so minimal as not to make the carpet off-spec or unacceptable with respect to color.

As will be clear to those skilled in the art, the dyeing parameters employed in dyeing the jute backing according to the invention process will vary depending on a number of interrelated factors such as: the type of dyeing process used, e.g. batch or continuous; the kinds and quantities of nylon face fibers and the type of jute present in the carpeting; the type and concentration of dyestuffs used in dyeing the face fibers and the jute backing; the kind and quantity of imidazoline reserving agent employed; and, finally, the dyeing parameters themselves; and that, hence, such parameters can not be specified with exactness. Bearing in mind this caveat, the dyeing parameters employed with the imidazoline salts and/or quaternaries, are, for the most part conventional, and are, typically, as hereinafter described (based for clarity of expression on a batch dyeing process).

Thus, the invention process may be used with virtually all cationic dyestuffs particularily suited to and recommended for dyeing the jute backing of carpeting made up in part (but usually in total) of multilevel nylon face fibers subject to staining. Such cationic jute dyestuffs are well known and constitute no part per se of the invention process. The quantity of jute dyestuff is chosen to give the desired shade. The dyeing times required to obtain acceptable color yields on the jute are generally of the same magnitude, although, in some instances, longer times may be required.

The liquor ratio of the dye bath, likewise, is conventional and not narrowly critical and typically may vary from about 10:1 to 40:1. Lower or higher ratios may be used if desired. Generally, in good dyeing practice, any residual unfixed face fiber dyes and adjuvants are removed by rinsing after the face is dyed and before dyeing the jute backing.

The quantity of the imidazoline reserving agent employed (on a 100% solids basis) may vary from as little as about 0.10 up to about 2.0% maximum on the total carpet weight, with about 0.25–1.0% usually being required for satisfactory results. While, with some types of jute dyes and/or imidazoline compounds, the reserving agent may be added just before or concurrently with the jute dye, maximum efficiency generally is obtained when it is added to the bath first, and the carpeting pretreated for some finite period, such as 5 to 30 minutes (until the reserving agent is essentially exhausted). Such pretreatment may also be required with nylon face fibers of some manufactures as hereinafter further described.

With respect to the dyeing temperature, it has been observed that temperatures of less than about 50°F are impractically slow, while temperatures in excess of about 90°F, in many instances, cause staining of the nylon face fibers. Thus, for most jute dyeings employing the invention reserving agents, dyeing temperatures in the range of about 60°–80°F will generally be found to provide the best compromise with respect to acceptable dyeing speed and absence of discernable staining of the face fibers.

In dyeing the jute with cationic dyes in the presence of the imidazoline reserving agents, a pH of about 3.0 to 7.5 may be used, with a pH of about 4 to 6 usually being optimium depending upon the type of jute dyestuff being used. At a pH of less than 3.0, dyeing of the jute may be retarded, while pH's appreciably more alkaline than 7.5 can reduce the solubility of cationic jute dyestuffs and the solubility and stability of the imidazoline reserving agents (cause partial hydrolysis of the imidazoline cation to the amide). The pH of the dye bath may be adjusted with any acid, base or buffer typically used in dyeing jute with cationic dyes, and the anions of acids and buffers used may be the same or different than the anions present in the imidazoline reserving agents. Typically, acetic acid is used for safety reasons and because of its ability to give desired pH's at a wide range of concentrations. With the polyamide fibers of some manufacturers, best results are obtained by pretreating the carpet with the imidazoline reserving agent at an alkaline pH for some period of time, such as 5 to 20 minutes, and then reducing the pH to an acid pH, usually 4–6 for most jute dyes, prior to adding the jute dye.

Other dyeing adjuvants conventionally used in dyeing carpet jute backing may also be used, so long as the kinds and quantities are chosen so as not to negate the desired anti-staining effect of the imidazoline reserving agents.

While the foregoing description and the following examples have been directed to dyeing jute-backing by a batch process for the sake of clarity and explanation, it will be appreciated that the same parameters are generally applicable to continuous dyeing procedures although some modifications and adjustments may be necessary due to the differences inherent in the two processes, as will be readily apparent to the skilled artisan, and that the invention process can be used with equal facility for continuous dyeing processes.

Further, in the same vein, it will be obvious to those skilled in the art that the invention process is equally applicable to carpets containing in part face fibers other than polyamides, so long as they are compatible with the dyes and dyeing procedures used for the carpet face and backing. Additionally, it will be apparent from the foregoing description and following examples that the process is applicable to dyeing the jute backing of carpeting wherein all the face fibers have been pre-dyed or only some have been; or, in some instances, even where none have been pre-dyed, as, for example, From the data in the Table, it can be seen that the imidazoline compounds of the invention process effectively prevent staining of the nylon face fibers (either dyed or undyed) by the three jute dyes evaluated. Further, in all the examples acceptable color yields on the jute-backings were obtained. Conversely, in all the controls, where no reserving agent was used, all three jute dyestuffs caused heavy staining of both the dyed and undyed carpet face fibers.

Effectiveness of Imidazoline Compounds as Reserving Agents in Dyeing Jute Backing of Carpeting Having Multilevel Nylon Face Fibers

| Example | Reserving Agent | Face Fibers Pre-dyed | Jute[1] Dye | Staining of Face Fibers by Jute Dye |
|---|---|---|---|---|
| 1 | di-[1-(2-hydroxyethyl)-2-heptadecylene imidazoline] sulfate[2] | No | R | Hardly Discernible |
| 2 | " | No | B | " |
| 3 | " | No | G | " |
| 4 | " | Yes | R | Not Discernible |
| 5 | " | Yes | B | " |
| 6 | " | Yes | G | " |
| 7 | 1-(2-hyroxyethyl)-1-ethyl-2-heptadecylene imidazoline ethosulfate[3] | No | R | Hardly Discernible |
| 8 | " | Yes | R | Not Discernible |
| Control | | | | |
| A | None Used | No | R | Heavy |
| B | " | No | B | " |
| C | " | No | G | " |
| D | " | Yes | R | " |
| E | " | Yes | B | " |
| F | " | Yes | G | " |

Footnotes
[1] 0.25% jute dye was used for each example and control.
 Code for dyes used:
  R = C.I. Basic Violet 16
  B = C.I. Basic Blue 9
  G = C.I. Basic Green 4
[2] Three percent of an aqueous solution of the imidazoline compound having 45% solids and a pH of 6.5 was used. The compound was prepared by reacting in water slightly in excess of one mole of sulfuric acid with two moles of the condensation/cyclization product of one mole of 2-hydroxyethyl ethylene diamine and one mole of a technical grade oleic acid (85% oleic acid and 15% of other hydrocarbonoic acids having both less than and more than 18 carbons).
[3] Three quarters percent of the quaternization product of one mole of diethyl sulfate and one mole of the condensation/cyclization product described in Footnote 2.

when the face fibers are to be dyed after the jute backing.

EXAMPLES

In the following examples, set forth to illustrate the practice of the present invention, the amounts of chemicals and dyes used are expressed in percent by weight based on 100 percent by weight of the total carpeting (i.e. backing and face fibers).

A jute-backed carpeting having a mixture of two anionic-dyeable nylon face fibers (DuPont 854 and 855 fibers) and one cationic-dyeable nylon face fiber (DuPont 857 fiber) was used in all the examples and controls. In some of the examples and controls the face fibers of the carpet were undyed while in others the fibers were dyed with 0.05% C.I. Acid Red 266 (an anionic dye) and 0.05% C.I. Basic Yellow 11 (a cationic dye). This low level was used to accentuate any staining that might occur. The jute backing was dyed in both the examples and controls by the following procedure. The bath (40:1 liquor ratio) was set at 70°F with the type and quantity of imidazoline compound shown in the Table and acetic acid to a pH of 4.5, and the carpet circulated for 10 minutes. Then 0.25% of the jute dye, shown in the Table and predissolved in a small amount of warm water, was added. The carpet was run for 15 minutes at 70°F and then rinsed thoroughly and dried. The staining of the face fibers was visually determined, and is compiled in the Table.

What is claimed is:
1. In a process of dyeing with a cationic dye the backing of a jute-backed carpeting having multilevel nylon face fibers, the improvement which comprises; dyeing the jute backing in the presence of a quantity of an imidazoline compound preventing discernible staining of the face fibers, said compound having the general formula:

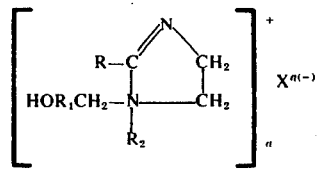

wherein:
R is a hydrocarbon radical having 15 to 17 carbon atoms,
$R_1$ is a

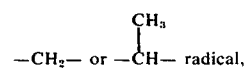

$R_2$ is hydrogen, an unsubstituted or hydroxy-substituted aliphatic hydrocarbon radical having 1 to 6 carbon atoms or a benzyl radical,
X equals a water-soluble anion, and $a$ is a number equal to the ionic valence of the anion, X.

2. The process of claim 1 wherein the carpeting is treated with the imidazoline compound for a finite period before dyeing the jute backing.

3. The process of claim 1 wherein $R_2$ is hydrogen.

4. The process of claim 1 wherein $R_2$ is an unsubstituted or hydroxy-substituted aliphatic hydrocarbon radical having 1 to 6 carbon atoms or a benzyl radical.

5. The process of claim 1 wherein $R_1$ is a — $CH_2$ — radical.

6. The process of claim 5 wherein R is a hydrocarbon radical having 17 carbon atoms.

7. The process of claim 6 wherein the carpeting is treated with the imidazoline compound for a finite period before dyeing the jute backing.

8. The process of claim 5 wherein R is a heptadecylene radical and $R_2$ is hydrogen.

9. The process of claim 8 wherein the carpeting is treated with the imidazoline compound for a finite period before dyeing the jute backing.

10. The process of claim 5 wherein R is a heptadecylene radical, $R_2$ is a methyl or ethyl radical, and $X^-$ is a methosulfate anion when $R_2$ is a methyl radical and an ethosulfate anion when $R_2$ is an ethyl radical.

11. The process of claim 10 wherein the carpeting is treated with the imidazoline compound for a finite period before dyeing the jute backing.

* * * * *